United States Patent [19]

Yamane et al.

[11] Patent Number: 4,935,351
[45] Date of Patent: Jun. 19, 1990

[54] PROCESS FOR PREPARING OLIGOPEPTIDE

[75] Inventors: Kunio Yamane, Niihari; Hisato Yamazaki, Himeji; Kazutaka Ohmura, Kashiwa; Teruaki Shiroza, Ichihara; Takashi Furusato, Tsukuba, all of Japan

[73] Assignees: Kunio Yamane, Ibaraka; Daicel Chemical Industries, Ltd., Sakai; The Calpis Food Industry Co., Ltd., Tokyo; Oji Corn Starch Co., Ltd., Tokyo; Nissan Chemicals Industries, Ltd., Tokyo, all of Japan

[21] Appl. No.: 756,522

[22] Filed: Jul. 18, 1985

[30] Foreign Application Priority Data

Jul. 27, 1984 [JP] Japan .................. 59-156562

[51] Int. Cl.$^5$ .............. C12P 21/00; C12P 21/02; C12N 1/20; C12N 15/00
[52] U.S. Cl. ................ 435/69.4; 435/252.31; 435/69.8; 935/9; 935/11; 935/14; 935/74
[58] Field of Search ............ 435/68, 172.3, 320, 435/70, 253, 252.31; 935/14, 29, 47, 48, 51, 72, 74

[56] References Cited

U.S. PATENT DOCUMENTS 4,411,994 10/1983 Gilbert et al. .................. 435/172.3
4,565,785 1/1986 Gilbert et al. .................. 435/172.3

FOREIGN PATENT DOCUMENTS 0006694 9/1980 European Pat. Off. .
0035384 9/1981 European Pat. Off. ......... 435/172.3
0036259 9/1981 European Pat. Off. .
2091268 7/1982 European Pat. Off. .

OTHER PUBLICATIONS

Kumarev, V. et al, *FEBS Letters*, vol. 114, No. 2, pp. 273-277, Jun. 1980.
Villa-Komaroff, L. et al, *Proc. Natl. Acad. Sci.*, vol. 75, pp. 3727-3731, 1978.
Cloning and Expression of a Bacillus coagulans Amylase Gene in *Escherichia coli*, MGG, Mol Gen Genet 1982, 186(4), pp. 507-511.
A *Bacillus subtilis* Secretion Vector System Derived from the *B. subtilis* α-Amylase Promoter and Signal Sequence Region, and Secretion of *Escherichia coli* β-Lactamase by the Vector System, Journal of Biochemistry, vol. 95, No. 1, 1984, pp. 87-93.
*Bacillus subtilis* Secretion Vectors for Proteins and Oligopeptides Constructed from B. subtilis α-Amylase Genes, Mol Biol Microb Differ, Proc Int Spore Conf, 9th 1984 (Pub 1985), pp. 117-123.
Nucleotide Sequence of the Promoter and $NH_2$-Terminal Signal Peptide Region of Bacillus subtilis α-Amylase Gene Cloned[2] in pUB110, Biochemical and Biophysical Research Communications, vol. 112, No. 2, 4/29/83, pp. 678-683.

*Primary Examiner*—Jayme A. Huleatt
*Attorney, Agent, or Firm*—Flynn, Thiel, Boutell & Tanis

[57] ABSTRACT

An oligopeptide is prepared by use of a vector wherein DNA coding for the intended oligopeptide has been introduced into a plasmid including a leader gene and an alpha-amylase structural gene.

3 Claims, 1 Drawing Sheet

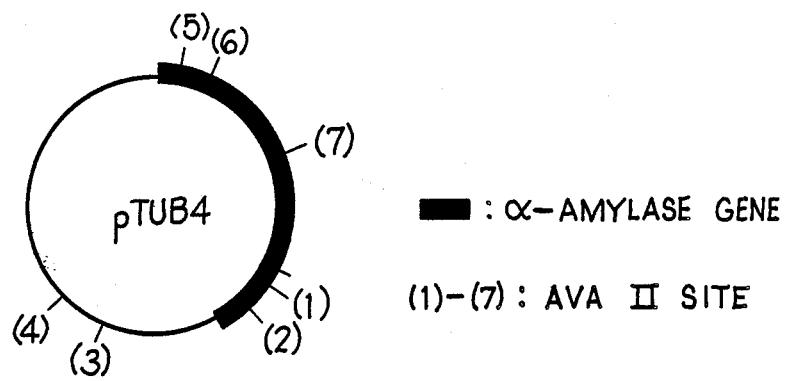

PROCESS FOR PREPARING OLIGOPEPTIDE

FIELD OF INDUSTRIAL APPLICATION

This invention relates to a process for preparing an oligopeptide with genetic engineering techniques. More particularly it relates to a process for preparing an oligopeptide wherein the oligopeptide is formed in cells and then is secreted out of the cells.

DESCRIPTION OF THE PRIOR ART

Conventional processes for preparing oligopeptides include a synthetic method and a biochemical method utilizing genetic engineering techniques.

The former method usually comprises introducing protective groups into amino or carboxyl groups of amino acids as a starting material before reaction, so it is necessary to remove said protective groups in the final step. However, it becomes more difficult to remove all of these protective groups with an increase in the length of the peptide chain. Thus, the obtained product is in the form of a mixture of the desired oligopeptide and other oligopeptides wherein some of the above protective groups remain. Therefore it is difficult to purify the desired oligopeptide. Furthermore, this synthetic method generally gives a poor yield.

Major examples of the latter method are those employing *Escherichia coli*. However, none of them allows the formed oligopeptide to be secreted out of the cells. Therefore, it is necessary to break the cells to collect the oligopeptide. The oligopeptide thus collected is generally in the form of a mixture with various peptides, so it is also difficult and troublesome to separate it.

SUMMARY OF THE INVENTION

As a result of our studies to overcome these problems of the prior art, we have completed the present invention.

Accordingly the present invention provides a process for preparing an oligopeptide characterized by using a vector wherein DNA coding for the desired oligopeptide is introduced into a plasmid including a leader gene and an α-amylase structural gene.

The process of the present invention is more particularly characterized by inserting the DNA coding for the desired oligopeptide into said α-amylase gene and secreting the fused protein comprising the α-amylase and oligopeptide out of the cells. In the process of the present invention, the desired product can be readily isolated and purified.

The DNA coding for the oligopeptide of the present invention may be derived from vital tissue cells. Alternately it may be prepared in a known manner, e.g., through synthesis by a solid phase triester method.

The oligopeptide produced by the invention preferably includes a hormone such as calcitonin, angiotensin I, bradykinin, somatostatin, insulin and luteotropic hormone, a precursor for each hormone mentioned before, and an antifungal peptide such as gramicidin A and mycobacillin.

The plasmid used in the present invention is usually selected from among those having an α-amylase gene and are prepared by cleaving a plasmid conventionally used in genetic engineering with a restriction enzyme to thereby open the ring and connecting an α-amylase gene to the ring-opened portion in a conventional manner. However those vectors derived from vital tissue cells are also usable so long as they have an α-amylase gene.

The α-amylase gene refers to those including an α-amylase structural gene, which codes for α-amylase protein, and a leader gene, which codes for a signal peptide for secreting the α-amylase out of the cells.

Out studies have revealed that the α-amylase activity of an α-amylase protein would be maintained when amino acid bonds of at least 436 molecules starting with the N terminal are sustained. Accordingly, a protein of a composition size capable of maintaining its α-amylase activity to which an oligopeptide is bonded, which is referred to as a fused protein, might exhibit an amylase activity.

Based on the above findings, we have attempted to develop a fused protein having an α-amylase activity by introducing DNA coding for the desired oligopeptide into an α-amylase gene.

BRIEF DESCRIPTION OF THE DRAWING

The FIGURE shows the cleavage sites on pTUB 4 for the restriction enzyme Ava II.

Now the present invention will be described in detail. It is to be understood that the invention is not intended to be limited thereby. Plasmid pTUB 4 is obtained by introducing an α-amylase gene into a well-known plasmid, pUB 110, derived from Staphylococcus.

In the abovementioned case, the leader gene portion of the α-amylase gene may be obtained, e.g., by the process disclosed in our preceding Japanese Patent Application No. 043826/1984 which corresponds to U.S. Pat. No. 4,690,898.

The plasmid pTUB 4 carries genetic information for kanamycin resistance originating from the pUB 110 and that for α-amylase, so that strains cloned with this plasmid may be readily selected.

Now the process for introducing the DNA coding for the desired oligopeptide into the plasmid pTUB 4 will be described.

Plasmid pTUB 4 may be cleaved with a restriction enzyme Ava II at seven sites. It has been revealed that five sites among them are present in the α-amylase structural gene while the residual two are present downstream of the α-amylase structural gene. Thus a fused protein having an α-amylase activity may be obtained by cleaving the plasmid pTUB 4 at an Ava II incision site present downstream.

Various DNA fragments may be obtained by partial digestion of the pTUB 4 with the restriction enzyme Ava II. Among these fragments, a plasmid ring-opened at the Ava II incision site present at the 1531th base sequence from the upperstream side of the α-amylase structural gene is selected and DNA coding for the desired oligopeptide is bonded thereto. Cloning of, e.g., *Bacillus subtilis* NA 64 strain (deposited with Fermentation Research Institute, FERM BP-423) with the vector thus obtained makes it possible to secrete the fused protein comprising the α-amylase and the oligopeptide out of the cells.

As the fused protein is secreted out of the cells with the signal peptide of α-amylase, it can be very readily isolated. After removing the cells, the fused protein may be purified in a conventional manner for the purification of α-amylase. The fused protein thus obtained is treated in an appropriate manner to give fragments of oligopeptides. The desired oligopeptide may be readily purified by taking advantage of the properties thereof.

PREFERRED EMBODIMENT OF THE INVENTION

To further illustrate the present invention, the following Example will be given.

EXAMPLE

Plasmid pUB 110 was treated with a restriction enzyme BamHI and an α-amylase gene derived from *B. subtilis* NA 64 strain was inserted into the ring-opened plasmid thus obtained to give plasmid pTUB 4. The pTUB 4 was subjected to partial digestion with a restriction enzyme Ava II and subsequently a plasmid ring-opened at site (1) as shown in the FIGURE was taken out by electrophoresis.

The base sequence in the neighborhood of the incision site (1) is as follows:

—AAAGCCGTTTATCAAATCAATAA<u>TGGACC</u>AGAC—
<u>Ava II incision site</u>

After incision with Ava II, Hind III linker was bonded to the incision site to give the following DNA sequence:

—AAAGCCGTTTATCAAATCAATAATGGACC<u>AAGCTT</u>GGAC—
<u>Hind III linker</u>

On the other hand, DNA coding for angiotensin I, known as a human hormone, was synthesized by a solid phase triester method. The DNA thus synthesized corresponded to the following amino acid sequence:

Met—Asp—Arg—Val—Tyr—Ile—His—Pro—
Phe—His—Leu

Methionine was incorporated to readily take out the angiotensin I by a CNBr treatment as described hereinbelow. A termination codon was bonded to the downstream side of the base sequence coding for leucine in the synthetic DNA. Hind III sites were further bonded to the down- and upperstream sides of the synthetic DNA. The synthetic DNA thus obtained was treated with the Hind III as described above wherein Hind III linker was bonded to pTUB 4, thus adding the former to the ring-opened site of the latter to give the following base sequence:

—AAAGCCGTTTATCAAATCAATAATGGACC<u>AAGCTT</u>G
<u>Hind III</u>

<u>ATG</u> GATAGGGTGTACATCCATCCGTTCCATCTG <u>TAG</u> <u>TGA</u>
Met     Angiotensin I                        Term Term <u>AGCTT</u>GGAC—
<u>Hind III</u>

The obtained vector wherein the DNA coding for angiotensin I was bonded to pTUB 4 was introduced into the *B. subtilis* NA 64 strain, thus selecting colonies exhibiting kanamycin resistance. Subsequently colonies including the angiotensin gene were selected by colony hybridization. The strains thus obtained were cultured to produce a fused protein of α-amylase and angiotensin I. Similar to the α-amylase secreted out of cells by the signal peptide as described above, the formed fused protein was secreted out of the cells. After removing the cells, ammonium sulfate was added to the medium to thereby sediment the protein, which was then dialyzed and passed through a DEAE-cellulose column twice. Thus the fused protein was obtained at a yield of 90% or above. The fused protein can be cleaved at methionine portions by treating with CNBr. The fused protein may be divided into several peptides by treating with CNBr and a peptide comprising 17 amino acids as the minimum unit may be obtained from the protein originating from α-amylase. Angiotensin I is a peptide comprising 10 amino acids as mentioned above. Thus angiotensin I could be purified by treating the mixture of peptides obtained by the CNBr treatment with the DEAE-cellulose column.

The angiotensin I thus obtained exhibited its inherent bioactivity. As a result of the analysis of the plasmid of strains producing the fused protein, the abovementioned DNA sequence was confirmed.

The symbols used in the above Example stand for the following compounds:

Met methionine
Asp asparatic acid
Arg arginine
Val valine
Tyr tyrosine
Ile isoleucine
His histidine
Pro proline
Phe phenylalanine
Leu leucine
A adenine
T thymine
G guanine
C cytosine.

The embodiments of the invention in which an exclusive property or privilege is claimed are defined as follows:

1. A process for preparing an oligopeptide having up to 10 amino acids comprising the steps of:
   (1) inserting DNA coding for the oligopeptide having up to 10 amino acids into pTUB 4, which has a leader gene and an α-amylase structural gene sequence obtained from *Bacillus subtilis* NA 64, at site 1 shown in the FIGURE;
   (2) introducing the pTUB 4 into a *Bacillus subtilis* cell and obtaining a transformed *Bacillus subtilis* cell;
   (3) culturing said transformed *Bacillus subtilis* cell;
   (4) secreting a fused protein comprising the α-amylase and the oligopeptide out of the transformed *Bacillus subtilis* cell; and
   (5) separating the oligopeptide from the fused protein.

2. The process of claim 1, wherein said oligopeptide is selected from the group consisting of angiotensin I and bradykinin.

3. A process for preparing angiotensin I comprising the steps of:
 (1) inserting DNA coding for angiotensin I into pTUB 4 at site 1 shown in the FIGURE;
 (2) introducing the pTUB 4 into a *Bacillus subtilis* cell and obtaining a transformed *Bacillus subtilis* cell;
 (3) culturing said transformed *Bacillus subtilis* cell;
 (4) secreting a fused protein comprising the α-amylase and angiotensin I out of the transformed *Bacillus subtilis* cell; and
 (5) separating the angiotensin I from the fused protein.

* * * * *